US008696716B2

(12) United States Patent
Kartalian et al.

(10) Patent No.: US 8,696,716 B2
(45) Date of Patent: Apr. 15, 2014

(54) FIXATION AND ALIGNMENT DEVICE AND METHOD USED IN ORTHOPAEDIC SURGERY

(75) Inventors: George Kartalian, Great Falls, VA (US); Ali Siam, Stoughton, MA (US)

(73) Assignee: ProActive Orthopedics, LLC, Great Falls, VA (US)

( * ) Notice: Subject to any disclaimer, the term of this patent is extended or adjusted under 35 U.S.C. 154(b) by 932 days.

(21) Appl. No.: 12/184,704

(22) Filed: Aug. 1, 2008

(65) Prior Publication Data

US 2009/0036893 A1 Feb. 5, 2009

Related U.S. Application Data

(60) Provisional application No. 60/953,657, filed on Aug. 2, 2007.

(51) Int. Cl.
*A61B 17/84* (2006.01)
*A61B 17/88* (2006.01)

(52) U.S. Cl.
USPC ........... 606/300; 606/313; 606/315; 606/320; 606/327; 606/331; 606/105

(58) Field of Classification Search
USPC ............... 606/300–321, 326–328, 331, 105, 606/65–66; 623/13.14
See application file for complete search history.

(56) References Cited

U.S. PATENT DOCUMENTS

| | | | | |
|---|---|---|---|---|
| 3,312,139 A | * | 4/1967 | Di Cristina | 411/54 |
| 4,409,974 A | | 10/1983 | Freedland | |
| 4,456,005 A | * | 6/1984 | Lichty | 606/60 |
| 4,688,561 A | * | 8/1987 | Reese | 606/64 |
| 4,796,612 A | * | 1/1989 | Reese | 606/324 |
| 4,858,601 A | * | 8/1989 | Glisson | 606/916 |
| 5,061,137 A | * | 10/1991 | Gourd | 411/510 |
| 5,102,276 A | * | 4/1992 | Gourd | 411/392 |
| 5,167,664 A | * | 12/1992 | Hodorek | 606/306 |
| 5,217,462 A | * | 6/1993 | Asnis et al. | 606/916 |
| 5,250,049 A | * | 10/1993 | Michael | 606/324 |
| 5,529,075 A | * | 6/1996 | Clark | 128/898 |
| 5,827,285 A | * | 10/1998 | Bramlet | 606/60 |
| 5,993,486 A | * | 11/1999 | Tomatsu | 623/13.11 |
| 6,283,973 B1 | | 9/2001 | Hubbard et al. | |
| 6,348,053 B1 | | 2/2002 | Cachia | |
| 6,458,134 B1 | * | 10/2002 | Songer et al. | 606/304 |
| 6,464,706 B1 | * | 10/2002 | Winters | 623/13.14 |
| 6,736,819 B2 | * | 5/2004 | Tipirneni | 606/916 |
| 6,887,243 B2 | | 5/2005 | Culbert | |

(Continued)

OTHER PUBLICATIONS

International Search Report and Written Opinion corresponding to the PCT/US08/71961 application dated Oct. 27, 2008.

(Continued)

*Primary Examiner* — Michael T Schaper
(74) *Attorney, Agent, or Firm* — Muir Patent Consulting, PLLC

(57) ABSTRACT

Surgical anchoring systems and methods are employed for the correction of bone deformities. The anchoring system and its associated instrument may be suitable for surgical repair of hallux valgus, tarsometatarsal sprains, ankle ligament reconstruction, spring ligament repair, knee ligament reinforcement, acromioclavicular sprains, coracoclavicular sprains, elbow ligament repair, wrist and hand ligamentous stabilization or similar conditions. The anchoring system may include a fixation system for anchoring two or more sections of bone or other body parts and a system for aligning of one section relative to another section.

44 Claims, 9 Drawing Sheets

Panel I

Panel II

(56) References Cited

U.S. PATENT DOCUMENTS

| | | | |
|---|---|---|---|
| 6,890,333 B2 | 5/2005 | von Hoffmann et al. | |
| 6,908,465 B2 | 6/2005 | von Hoffmann et al. | |
| 6,942,668 B2 | 9/2005 | Padget et al. | |
| 7,008,428 B2 | 3/2006 | Cachia et al. | |
| 7,070,601 B2 | 7/2006 | Culbert et al. | |
| 7,097,647 B2 | 8/2006 | Segler | |
| 7,175,667 B2 | 2/2007 | Saunders et al. | |
| 7,291,175 B1 | 11/2007 | Gordon | |
| 7,326,211 B2 | 2/2008 | Padget et al. | |
| 7,625,395 B2* | 12/2009 | Muckter | 606/300 |
| 7,875,058 B2* | 1/2011 | Holmes, Jr. | 606/232 |
| 7,951,198 B2* | 5/2011 | Sucec et al. | 623/13.11 |
| 7,955,388 B2* | 6/2011 | Jensen et al. | 623/13.14 |
| 8,277,459 B2* | 10/2012 | Sand et al. | 606/96 |
| 8,425,554 B2* | 4/2013 | Denove et al. | 606/232 |
| 2001/0049529 A1* | 12/2001 | Cachia et al. | 606/72 |
| 2002/0198527 A1* | 12/2002 | Muckter | 606/73 |
| 2003/0236555 A1* | 12/2003 | Thornes | 606/232 |
| 2004/0138665 A1* | 7/2004 | Padget et al. | 606/72 |
| 2004/0199165 A1* | 10/2004 | Culbert et al. | 606/75 |
| 2004/0260297 A1* | 12/2004 | Padget et al. | 606/72 |
| 2005/0177167 A1* | 8/2005 | Muckter | 606/73 |
| 2005/0187555 A1* | 8/2005 | Biedermann et al. | 606/72 |
| 2005/0240187 A1* | 10/2005 | Huebner et al. | 606/69 |
| 2005/0281633 A1* | 12/2005 | Mercer | 411/45 |
| 2006/0235410 A1* | 10/2006 | Ralph et al. | 606/72 |
| 2006/0271054 A1* | 11/2006 | Sucec et al. | 606/73 |
| 2006/0276793 A1* | 12/2006 | Berry | 606/69 |
| 2007/0162124 A1* | 7/2007 | Whittaker | 623/13.14 |
| 2008/0172097 A1* | 7/2008 | Lerch et al. | 606/324 |
| 2008/0177291 A1* | 7/2008 | Jensen et al. | 606/151 |
| 2008/0208252 A1 | 8/2008 | Holmes | |
| 2009/0131936 A1* | 5/2009 | Tipirneni et al. | 606/64 |
| 2009/0210016 A1* | 8/2009 | Champagne | 606/309 |
| 2009/0228049 A1* | 9/2009 | Park | 606/301 |
| 2010/0076504 A1* | 3/2010 | McNamara et al. | 606/86 R |
| 2010/0211071 A1* | 8/2010 | Lettmann et al. | 606/60 |
| 2010/0249855 A1* | 9/2010 | Bless | 606/305 |
| 2011/0077656 A1* | 3/2011 | Sand et al. | 606/96 |
| 2011/0118780 A1* | 5/2011 | Holmes, Jr. | 606/232 |
| 2011/0130789 A1* | 6/2011 | Shurnas et al. | 606/232 |
| 2011/0224738 A1* | 9/2011 | Sucec et al. | 606/315 |
| 2012/0016426 A1* | 1/2012 | Robinson | 606/328 |
| 2012/0016428 A1* | 1/2012 | White et al. | 606/86 R |
| 2012/0071935 A1* | 3/2012 | Keith et al. | 606/328 |
| 2012/0101502 A1* | 4/2012 | Kartalian et al. | 606/74 |
| 2012/0330322 A1* | 12/2012 | Sand et al. | 606/96 |
| 2013/0030475 A1* | 1/2013 | Weiner et al. | 606/306 |
| 2013/0030480 A1* | 1/2013 | Donate et al. | 606/328 |
| 2013/0138150 A1* | 5/2013 | Baker et al. | 606/232 |
| 2013/0158609 A1* | 6/2013 | Mikhail et al. | 606/305 |
| 2013/0184708 A1* | 7/2013 | Robinson et al. | 606/60 |
| 2013/0245700 A1* | 9/2013 | Choinski | 606/300 |
| 2013/0245701 A1* | 9/2013 | Kartalian et al. | 606/300 |

OTHER PUBLICATIONS

Foot & Ankle International, "The Arthrex, TightRope™ Fixation System". 2007.

Timothy Charlton, M.D."ZipTight™ Fixation System, featuring Zip Loop Technology: Ankle Syndesmosis". Surgical Protocol, Biomet Sports Medicine. Mar. 2009.

Coughlin, et al. "Proximal metatarsal osteotomy and distal soft tissue reconstruction as treatment for hallux valgus deformity". Keio J Med 2005; 54 (2): 60-65. Apr. 21, 2005.

* cited by examiner

Panel I   Panel II

FIXATION AND ALIGNMENT DEVICE AND METHOD USED IN ORTHOPAEDIC SURGERY

CROSS-REFERENCES TO RELATED APPLICATIONS

This application is related to and claims benefit under 35 U.S.C. §119(e) to provisional application Ser. No. 60/953,657, filed on Aug. 2, 2007, the disclosure of which is herein incorporated by reference in its entirety herein.

BACKGROUND OF THE INVENTION

1. Field of the Invention

The invention relates generally to an anchoring system and an associated surgical instrument, which may have multiple uses in orthopedic surgery such as joint stabilization, bunion correction, ligament reconstruction and similar procedures. More particularly, the anchoring system of the invention may include a system for anchoring two or more body parts together and a system for aligning movement of one anchored body parts relative to another.

2. Related Art

Various devices and methods have been used in the prior art for bone realignment, fixation of the bones or bone portions, and ligament reconstruction repair in order to correct for various orthopedic conditions, such as hallux valgus, tarsometatarsal sprains, ankle ligament reconstruction, and spring ligament repair.

Hallux valgus is a common foot disorder of several etiologies, which can lead to significant foot pain and deformity. Hallux valgus may be defined as a static subluxation of the first metatarsophalangeal (MTP) joint with lateral deviation of the great toe and medial deviation of the first metatarsal. Moreover, the condition may be accompanied by rotational pronation of the great toe in severe cases. The skeletal deformity results in increased sensitivity to any pressure created by contact. The condition may be self-perpetuating because the pressure that the bunion creates against the patient's footwear causes the metatarsal bone at the point of contact to thicken. A direct result of the thickening of the head of the metatarsal increases the size of the resulting bunion, which increases the severity of the condition and patient discomfort associated with the condition.

One of the most common causes of hallux valgus is prolonged deformation of the foot caused by wearing shoes that do not fit properly, such as high-heeled shoes and narrowly pointed toe shoes. Here, the big toe is forced into an abnormal orientation for a long period of time, which eventually stretches out the joint capsule and promotes abnormal migration of the muscles. There are other factors that may contribute to hallux valgus, which include rounded unstable MTP joint surfaces and oblique joint surfaces located at the proximal first metatarsal joint.

The initial symptom of hallux valgus may be pain at the joint prominence when wearing certain shoes. The capsule may be tender at any stage. Later symptoms may include a painful warm, red, cystic, movable fluctuant swelling located medially and swelling and mild inflammation affecting the entire joint which is more circumferential.

The diagnosis of a hallux valgus condition may include accurately defining a number of critical measurements through the use of x-rays taken of the foot's bone structure. First, the intermetatarsal angle (IM angle) may be determined. The IM angle may be defined by the relationship of the first metatarsal shaft compared to the line of the second metatarsal shaft. Under normal conditions, the IM angle may be in the range of about 6 degrees to about 9 degrees. Secondly, the hallux valgus angle (HV angle), which may be defined by the angle of the line created at the MTP joint between the first metatarsal bone shaft and the first phalangeal bone shaft may be determined. Under normal conditions, the HV angle may be in the range of about 9 degrees to 10 degrees. The HV angle may be considered to be in the abnormal range if the measurements are greater than about 15 degrees. Finally, the condition of the MTP joint may be evaluated to determine whether there has been a lateral subluxation of the joint. The combined evaluation of these and other factors will determine the course of action to be taken.

There are numerous types of surgical procedures that may be employed to correct a bunion. Currently, the state of the art consists of various osteotomies to realign the first metatarsal (MT) and the first MTP joint. These procedures do not function through the axis of deformity. Rather, they attempt to realign the bone and joint by translating and rotating the MT through a location that is accessible and minimizes complications. However, there are several complications related to altering blood supply of the MT, and to altering the length and position of the MT associated with this surgical procedure. Furthermore, the surgical exposure required, the trauma to and shortening of the bone from sawing, and the prolonged healing time required all lead to less than satisfactory results.

One alternative to using an osteotomy to treat hallux valgus is to perform a corrective arthrodesis of the tarsometatarsal joint. The advantage of this approach is that the deformity is corrected where it is occurring, and allows for a powerful correction of large deformities. The disadvantage, however, to this approach is that a normal joint is being sacrificed, which alters the subsequent biomechanics of the foot. Additionally, the surgical technique has been found to have a high rate of complications including a high rate of not healing properly.

BRIEF SUMMARY OF THE INVENTION

The invention provides an anchoring system and an associated instrument, and surgical methods to optimize the surgical correction of bone deformities from a biomechanical and biological standpoint that provides numerous advantages over conventional devices and techniques currently used for joint stabilization, bunion correction or ligament reconstruction surgery and similar procedures. The invention may be implemented in a number of ways.

According to one aspect of the invention, a surgical instrument to align bones and/or guide a surgical device may include a body having a first proximal arm and a second distal arm and a cannulated sleeve supported by one of said arms. The sleeve may be configured to guide a surgical device. The alignment device may be supported by the other of the arms. The alignment device may be configured and arranged to hold a bone in proper alignment for the surgical device. The instrument may also include an angle indicator and a locking clamp.

The cannulated sleeve may be removably attached to the one arm. Moreover, the cannulated sleeve may function as a drill guide and the surgical device may be a drill. The alignment device may include an adjustable dorsal and plantar plate.

According to another aspect of the invention, a surgical method for repair of hallux valgus is provided. The surgical method may include entering the tissues of the foot affected with hallux valgus using at least one incision. The at least one incision may include making a medial incision at the first metatarsal, an incision lateral to the second metatarsal at its distal portion, and a first web space incision. Further, the method may include performing a soft-tissue release to release the abductor tendon, fibular sesamoid attachements and the lateral metatarsalphalangeal (MTP) joint capsule, shaving the exostosis, and stabilizing and reorienting a first metatarsal, which may be accomplished by placing the surgical instrument of the invention on the first and second metatarsal. The first proximal arm of the surgical instrument may be placed on the first metatarsal and the second distal arm of the surgical instrument may be placed on the second metatarsal.

The surgical method may also include creating a tunnel across the first metatarsal, creating a pilot hole in the second metatarsal, embedding an anchor in the pilot hole in the second metatarsal, and inserting an interference screw in the first metatarsal. The anchor may include anchor region and a connector region. Furthermore, the anchor region may be non-absorbable and/or osteogenic and fabricated from a material such as stainless steel, titanium, or other suitable metallic materials. Also, the anchor region may be bioabsorbable and fabricated from a material such as polylactic acid, bone allograft, and hydroxyapatite coral. The connector region of the anchor may be fabricated from a material such as human dermis, porcine intestinal mucosa, porcine intestinal mucosa, fetal bovine skin, porcine skin, cadeveric fascia, polytetrafluorethylene, polypropylene, marlex mesh, absorbable or a nonabsorbable suture, and umbilical tape, for example. Also, the anchor region may be osteogenic and coated with a bone growth factor. The interference screw may include at least one suture receiving portion and that may function to secure a reduction in the hallux valgus (HV) angle of the first toe. The interference screw may be bioabsorbable and may be fabricated from a material such as polylactic acid, bone allograft, and hydroxyapatite coral. The interference screw may be osteogenic and coated with a bone growth factor.

According to another aspect of the invention, a surgical anchor system for use in the repair of an orthopedic condition is provided. The anchor system may include an anchor having a collapsed position for delivery to a canal of a first bone and an expanded position for securing the anchor within the bone canal, and a connector extending between the anchor and a fixation device configured to be fixedly attached to a second body part. The orthopedic condition may be hallux valgus, tarsometatarsal sprains, ankle ligament reconstruction, spring ligament repair, knee ligament reinforcement, acromioclavicular sprains, coracoclavicular sprains, elbow ligament repair, and wrist and hand ligamentous stabilization.

The anchor may include two resilient arms made of a biocompatible material. Moreover, the anchor region may be bioabsorbable and may be fabricated from a material such as polylactic acid, bone allograft, and hydroxyapatite coral. The anchor region may also be osteogenic and coated with a bone growth factor. The connector region may be fabricated from a material such as human dermis, porcine intestinal mucosa, porcine intestinal mucosa, fetal bovine skin, porcine skin, cadeveric fascia, polytetrafluorethylene, polypropylene, marlex mesh, absorbable suture, nonabsorbable suture, and umbilical tape.

The fixation device may be an interference screw. The interference screw may be bioabsorbable and may be fabricated from a material such as polylactic acid, bone allograft, and hydroxyapatite coral. The interference screw may be osteogenic and coated with a bone growth factor. The interference screw may include at least one suture receiving portion that may function to secure a reduction in the HV angle between the first metatarsal and the proximal phalanx. The second body part may be a second bone. The first bone may be a first metatarsal and the second bone may be a second metatarsal.

According to another aspect of the invention, a surgical anchor system for use in the repair of an orthopedic condition may include a primary anchor adapted to engage a first bone, a secondary anchor adapted to engage a second bone, a connector component extending between said primary and secondary anchors, and at least one of said first anchor and said secondary anchor being connected to said connector component in one of a plurality of predetermined, lockable positions disposed along the length of said connection component.

The connection component may comprise a one-way or a two-way ratcheting mechanism. The ratcheting mechanism may comprise a mating engagement between an interior surface of the primary anchor and/or the secondary anchor and the connection component.

The primary anchor may be fixedly attached to the first bone by at least one of screw threads, barbs, loops, and cuffs. The primary anchor may comprise an expandable material having resilient arms to fix said primary anchor in place in the canal of the first bone.

The secondary anchor may be connected to the connection component via said ratcheting mechanism. The secondary anchor may be fixedly attached to the second bone by at least one of screw threads, barbs, loops, and cuffs. The secondary anchor may have a first portion disposed in a canal of the second bone and a second portion disposed against an outer surface of the second bone. The first bone may be a second metatarsal and the second bone may be the first metatarsal.

The primary anchor and the secondary anchor may be bioabsorable and may be fabricated from a material such as polylactic acid, bone allograft, and hydroxyapatite coral. The primary anchor and the secondary anchor may be non-bioabsorbable and may be fabricated from a material such as stainless steel and titanium. The primary anchor and the secondary anchor may be osteogenic and may be coated with a bone growth factor.

The connection component may be fabricated from a material such as human dermis, porcine intestinal mucosa, porcine intestinal mucosa, fetal bovine skin, porcine skin, cadeveric fascia, polytetrafluorethylene, polypropylene, marlex mesh, absorbable suture, non-absorable suture, and umbilical tape. The connection component may be fixedly attached to the primary anchor and/or the secondary anchor in at least one direction. The connection component may be fixedly attached to the primary and/or secondary anchor in two directions. The connection component may be pivotally attached to the primary anchor and/or the secondary anchor. The connection component functions to secure a reduction between the HV angle of the first metatarsal and a proximal phalanx.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification; illustrate embodiments of the invention and together with the detailed description serve to explain the principles of the invention.

No attempt is made to show structural details of the invention in more detail than may be necessary for a fundamental understanding of the invention and various ways in which it may be practiced.

DETAILED DESCRIPTION OF THE INVENTION

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. This, for example, a reference to "a capsule" is a reference to one or more capsules and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

BMP is bone morphogenetic protein
bFGF is basic fibroblast growth factor
GAMs are gene-activated matrices
IM is the intermetatarsal angle
HV is the hallux valgus angle
MT is metatarsal
MTP joint is metatarsophalangeal joint
PLA is polylactic acid The term "intermetatarsal angle" or "IM angle," as used herein generally refers to the angle that may be measured between the line of the first and second metatarsal shafts. In the normal foot, the IM angle is in the range of about 6 degrees to about 9 degrees. In a patient afflicted with hallux valgus, the IM angle is about 15 degrees.

The term "hallux valgus angle" or "HV angle," as used herein generally refers to the angle that may be measured between the line of the first metatarsal shaft and the proximal phalanx. In the normal foot, the HV angle is in the range of about 9 degrees to about 10 degrees. In a patient afflicted with hallux valgus, the HV angle is about 30 degrees.

The terms "active agent," "drug," "therapeutic agent," and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned that also induce the desired pharmacologic effect. In particular, the therapeutic agent may encompass a single biological or abiological chemical compound, or a combination of biological and abiological compounds that may be required to cause a desirable therapeutic effect.

By the terms "effective amount" or "therapeutically effective amount" of an agent as provided herein are meant a nontoxic but sufficient amount of the agent to provide the desired therapeutic effect. The exact amount required will vary from subject to subject, depending on the age, weight, and general condition of the subject, the severity of the condition being treated, the judgment of the clinician, and the like. Thus, it is not possible to specify an exact "effective amount." However, an appropriate "effective" amount in any individual case may be determined by one of ordinary skill in the art using only routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" individuals afflicted with hallux valgus, as the term "treating" is used herein, encompasses treatment of hallux valgus in a clinically symptomatic individual.

The terms "condition," "disease" and "disorder" are used interchangeably herein as referring to a physiological state that can be detected, prevented or treated by the surgical techniques, devices and/or therapeutic agent as described herein. Exemplary diseases and conditions in which the anchoring system, methods, and therapeutic agents of the invention may be used may include, but are not limited to, hallux valgus, Lis-Franc injury, midfoot sprains, flat feet, acromiocavicular sprains, coracoclavicular sprains, tarsalmetatarsal sprains, or similar conditions.

The term "patient" as in treatment of "a patient" refers to a mammalian individual afflicted with or prone to a condition, disease or disorder as specified herein, and includes both humans and animals.

The term "biomaterial," as used herein generally refers any suitable natural, synthetic material, absorbable, non-absorbable, or recombinant material such as extracellular matrix bioscaffolds, cadaveric fascia, suture-type materials, or umbilical tape that may be used as part of the anchoring system of the invention.

The term "bioabsorbable" as used herein generally may include a bioabsorbale material such as poly-D, L-lactic acid, polyethylene glycol, polydioxanone, polylactic acid, 70L/30DL polylactide, polyglycolide, poly(orthoester), calcium sodium metaphosphate, hydroxyapatite, calcium phosphate, polytetra fluoroethylene, collagen I, II, IX, X, and XI, durapatite, and hydrogel.

The terms "polymer" or "biopolymer," as used herein generally refer to a compound having two or more monomer units, and is intended to include linear and branched polymers, and copolymers, the term "branched polymers" encompassing simple branched structures as well as hyperbranched and dendritic polymers. The term "monomer" is used herein to refer to compounds that are not polymeric. "Polymers" or "biopolymers" herein may be naturally occurring, chemically modified, or chemically synthesized.

The term "cortex" as used herein, generally refers the outer wall of a bone.

The anchoring system of the invention may have multiple uses in orthropaedic surgery. In particular, the invention may be used in a surgical procedure for insertion of the anchoring system and an associated surgical instrument to facilitate proper insertion of the anchoring system. The anchoring system of the invention may include a system for aligning two or more body parts, such as sections of bone, ligaments, tendons, tissues, and the like, and a system for fixing one section of relative to another section. As such, the anchoring system, including the fixation system and an alignment system may be made of any biocompatible material, and specifically, a bioabsorbable material. Alignment may refer to any change in position along various geometric axes (X, Y and Z) in isolation or in concert. More particularly, the anchoring system and its associated instrument may be suitable for surgical repair of hallux valgus, tarsometatarsal sprains, ankle ligament reconstruction, spring ligament repair, knee ligament reinforcement, acromioclavicular sprains, coracoclavicular sprains, elbow ligament repair, wrist and hand ligamentous stabilization, and similar conditions.

Figure 1:
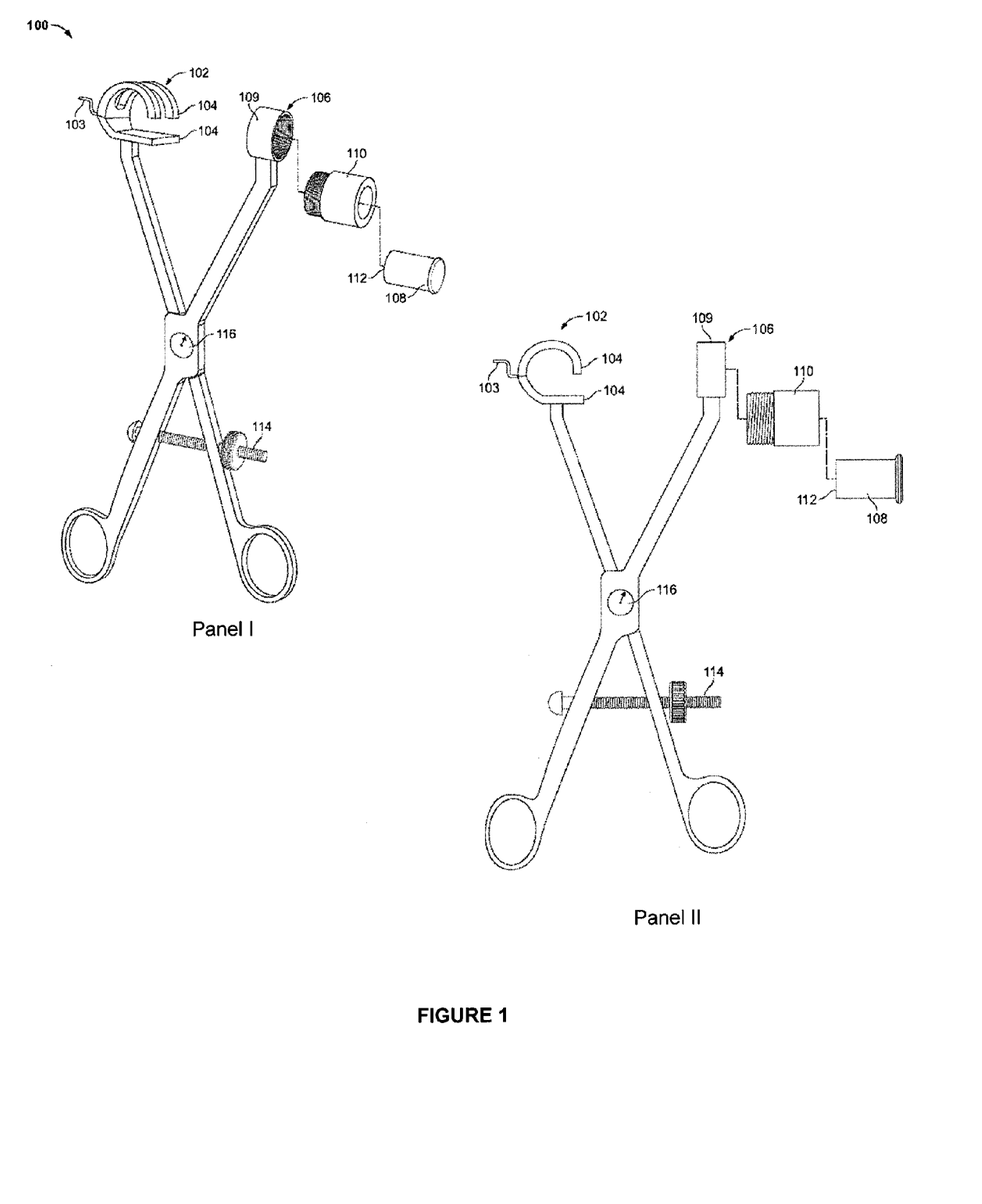
FIG. 1 is a schematic showing one embodiment of a surgical instrument constructed according to principles of the invention, which instrument may be employed to insert an anchoring system of the invention or similar device. Panel I is a side view of the surgical instrument constructed to principles of the invention and Panel II is a front view of the surgical instrument constructed to principles of the invention.

Referring to FIG. 1, a surgical instrument 100 is illustrated that may be employed for insertion of an anchor device of the invention suitable for the alignment and stabilization of the target bone(s). Instrument 100 may be fabricated from stainless steel, titanium, or any other material or combinations of material to produce an instrument that is relatively hard, impervious to damage by accidental contact with a drill bit, non-corrosive, and biocompatible. Instrument 100 may have a first end 102 and a second end 106, which are shown from different perspectives to better illustrate their features. End 102 may function as a caliper, which may be configured as a towel clip or configured to include two vertically spaced plates 104 that may function to center instrument 100 on the desired bone, such as a metatarsal. Thus, one of the plates may be curved or other shape to conform to the parts being clamped, and include two prongs as shown in FIG. 1. The plates may be spring biased towards each other by any means known in the art. Moreover, once the plates have been placed around the bone, the position of the plates may be secured by a locking mechanism 103, which may fix the relative positions of the plates by any conventional means.

Alternatively, the first arm 102 of the instrument 100 may use a cerclage wire around the metatarsal instead of the plates 104. Once the wire is passed around the metatarsal, each limb of the wire may be passed through cannulated guides on the second arm 102. The more distal, or lateral, guide may be a part of a curved plate that may rest along the plantar and lateral surface of the metatarsal. The more medial limb of the wire may pass through an adjustable guide that may slide down to the dorsal surface of the metatarsal and lock in place. This locking mechanism may provide secure fixation while centralizing the distal arm 102 along the second metatarsal regardless of variations in width.

The second end 106 may be configured as a cannulated sleeve 108 to function as a drill guide. Specifically, sleeve 108 may have an outer sleeve 110 and an inner sleeve 112. The sleeve 108 may be removably attached to ring 109 by a connection with its outer sleeve 110, such as by threads for engaging complementary threads on ring 109. The outer sleeve 110 may be attached to ring 109 by any other known mechanical connection such as interference fit, and the like. The instrument 100 may act as reduction forceps to align two bones or reduce the distance between the bones, as desired. Moreover, instrument 100 may allow for correction of any rotational deformity (pronation) when used for surgical correction of a bunion.

In a further embodiment, instrument 100 may include a locking clamp 114 to hold the instrument 100 in position once the final alignment of the bones has been achieved. The locking clamp may be fabricated and configured as understood by those skilled in the art. Furthermore, instrument 100 may include an automatic angle indicator 116 to provide the surgeon with an estimate of the angle between the bones requiring correction. Specifically, one skilled in the art appreciates that trigonometry may be used to estimate the angle between the two bones using known data regarding the length of the bones from x-rays or from anthropomorphic averages along with the final distance between the instrument arm 118 and instrument arm 120 to estimate the angle. The instrument 100 then may be suitably calibrated to show the angle between the bones.

In one embodiment, the anchoring system of the invention and an associated instrument for insertion of the anchoring system may be employed for surgical repair of hallux valgus or bunion correction. The surgical correction may involve a soft-tissue release, placement of instrument 100 on the first metatarsal and the second metatarsal to properly insert an anchoring and alignment system of the invention, properly aligning and securing the reduction of the IM angle of the first metatarsal, and subsequent removal of instrument 100, as described immediately below.

The surgical repair of hallux valgus may commence with a medial incision at the first metatarsal and an incision lateral to the second metatarsal at its distal portion followed by a web space soft-tissue release through a small dorsal incision, followed by placement of instrument 100. Specifically, the distal soft tissue procedure may involve release of the adductor hallucis and the flexor hallucis brevis as they are elevated from the lateral sesamoid and released from their attachment to the fibular side of the first proximal phalanx. The soft-tissue release may result in release of the adductor tendon, fibular sesamoid attachments, and the lateral MTP joint capsule, which aids in correction of the bones and placement of the surgical instrument 100. This is followed by a Silver bunionectomy to shave the exostosis, which results in further release of the medial soft tissue. Next, the surgical instrument 100 may be placed to the targeted location, which may be on two separate bones or across a joint requiring correction.

After the instrument 100 is placed on the bones and the bone is set in the desired orientation, the reduction or realignment may occur to the desired angle as estimated by the angle indicator 116. For example, first end 102 may be placed on the distal second bone (second metatarsal) and second end 106 may be placed on the proximal first bone (first metatarsal). The sleeve 108 on the proximal end of instrument 100 may be used as a drill guide. Initially, a first sleeve 108 having an inner diameter 112 in the range of about 3 millimeters (mm) to about 4 mm, which is capable of accommodating a large diameter drill, may be used as a guide to create a tunnel across the proximal first bone in line with the end 102. Subsequently, sleeve 108 is removed and replaced with a new sleeve 108 having a smaller inner diameter 112 in the range of about 1 mm to about 2 mm. The new sleeve 108 may then serve as a guide for a smaller diameter drill to make a pilot hole in the distal second bone.

Figure 2:
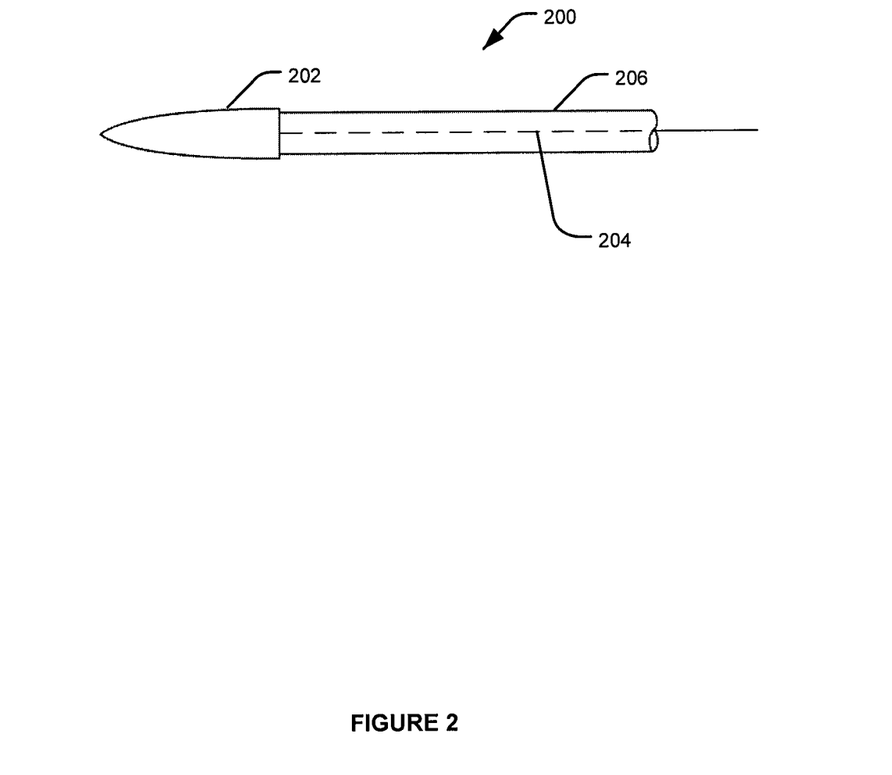
FIG. 2 is a schematic illustrating one embodiment of an anchoring system constructed according to principles of the invention.

In a further embodiment, a small anchor as depicted in FIG. 2 is set in the pilot hole created in the distal second bone. Referring to FIG. 2, anchor 200 includes an anchor region 202 and a connector region 204. The anchor region 202 may be capable of functioning as an intramedullary fixation device, a suspension fixation device, a drill and screw type fixation device or the like. If the anchor region 202 is an intramedullary type, it may have two arms that release in opposite directions within the bone canal to gain secure purchase. Alternatively, the anchor region 202 may be of a specific geometric shape that allows one-way passage through the cortical drill hole, but will subsequently become rigidly fixed within the bone canal once it passes through the cortex of the bone. The anchor region 202 may be non-absorbable and/or osteogenic and may be fabricated from, but not limited to stainless steel, titanium, and other suitable materials. Additionally, the anchor region 202 may be absorbable and/or osteogenic and may be fabricated from, but not limited to, polylactic acid, bone allograft, and hydroxyapatite coral.

In yet a further embodiment, the connector region 204, which is placed across the first and second metatarsals and functions to secure the reduction of the IM angle, may be fabricated from any suitable biocompatible material (biomaterial) and may be surrounded by a hollow sleeve 206. For example, the biomaterial may include any natural or synthetic materials such as Graff Jacket® (Wright Medical Technology), human dermis, Restore® (Depuy Orthopaedics), porcine intestinal mucosa, Cuffpath® (Arthrotek), porcine intestinal mucosa, TissueMend® (TEI Biosciences), fetal bovine skin, Permacol® (Tissue Science Laboratories), porcine skin, cadeveric fascia, polytetrafluoroethylene, polypropylene, marlex mesh, Ethibond®, FiberWire® (Mitek), any other absorbable and/or non-absorbable sutures, Arthrex®, and umbilical tape. The biomaterial 204 in communication with the anchor may be either tubular or flat. The length, shape, geometry and thickness of the biomaterial may be dependent upon usage. Moreover, hollow sleeve 206 may provide rigidity for placement if the anchor is passed through the first proximal bone and into the second distal bone. Further, the hollow sleeve 206 may be absorbable and may be fabricated out of, but not limited to, polylactic acid, bone allograft, and hydroxyapatite coral. After the anchor 200 is secured within the second bone, the hollow sleeve 206 may be removed and the biomaterial passed through the hole in the first proximal bone.

Figure 3:
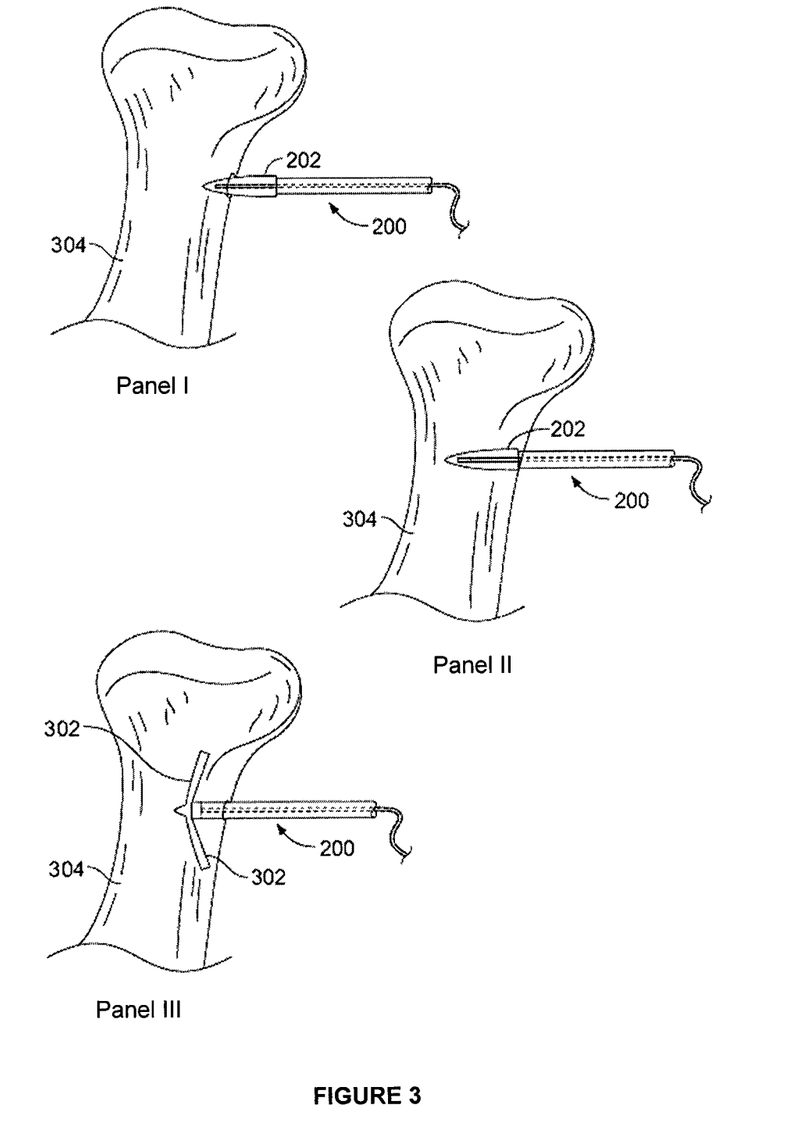
FIG. 3 schematically shows insertion of the anchoring system of the invention into the canal of the target bone. Panel I shows the anchoring system as it passes through the cortex of the bone. Panel II shows insertion of the anchoring system into the canal of the bone. Panel III shows the anchoring system securing itself within bone canal. In Panel III, the arms of the anchoring system are released in opposite directions to secure the system, according to principles of the invention.

FIG. 3 schematically shows the progression of setting an anchor 200 in the pilot hole created in the distal second bone. As shown in FIG. 3, the anchor region 202 is similar to an intramedullary fixation device having two arms 302 that release outwardly in opposite directions within the bone canal 304 to secure the anchor 200 in place. The arms 302 may be pushed out of the sleeve 206 mechanically, be formed of thermally activated materials such as nitinol, or expanded by any other means known in the art.

Figure 4:
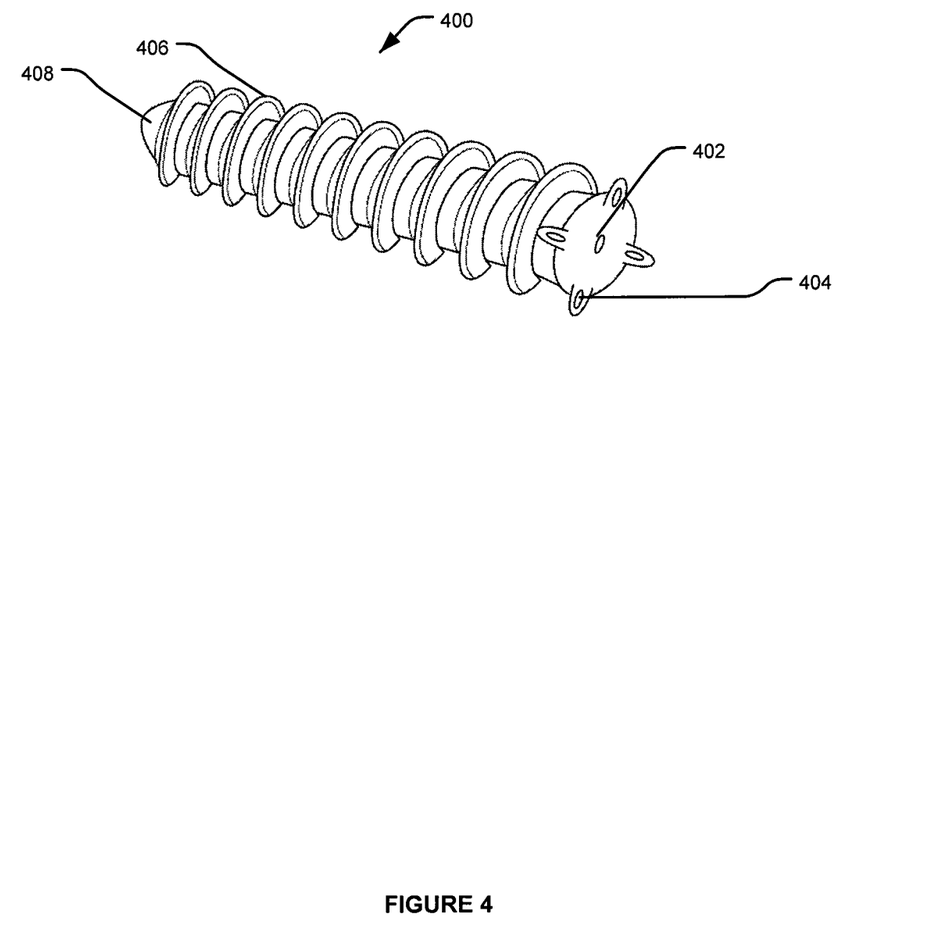
FIG. 4 is a schematic showing one embodiment of an interference screw constructed according to principles of the invention.

In yet a further embodiment, an interference screw may be inserted in the tunnel created in the proximal first bone after anchor 200 is properly engaged in the bone canal of the second distal bone. Turning to FIG. 4, an interference screw 400 is depicted having a throughbore 402 and a plurality of loops 404 or other attachment devices configured to allow a suture to pass through. Additionally, the screw 400 may be externally threaded 406 to engage the bone of the canal. Specifically, screw 400 may be threaded along its length and the threads may stop near its tip 408. As the biomaterial 204 is held at the desired length and tension, the screw may be inserted into the hole in the first proximal bone and may be advanced until a secure interference fit is achieved. The biomaterial 204 may be threaded through loops 404 to secure the repair. Once the screw 400 is set within the canal of the bone, instrument 100 may then be removed. After removal of the instrument 100, soft tissue repair may be initiated by tightening the capsular tissue to a fixed point into the attachment sites 404 of the screw 400. If the screw 400 is tightened further, tension and rotational correction may be achieved and the biomaterial 204 may be achieved to reinforce the repair, thereby resulting in a more secure repair.

Figure 5:
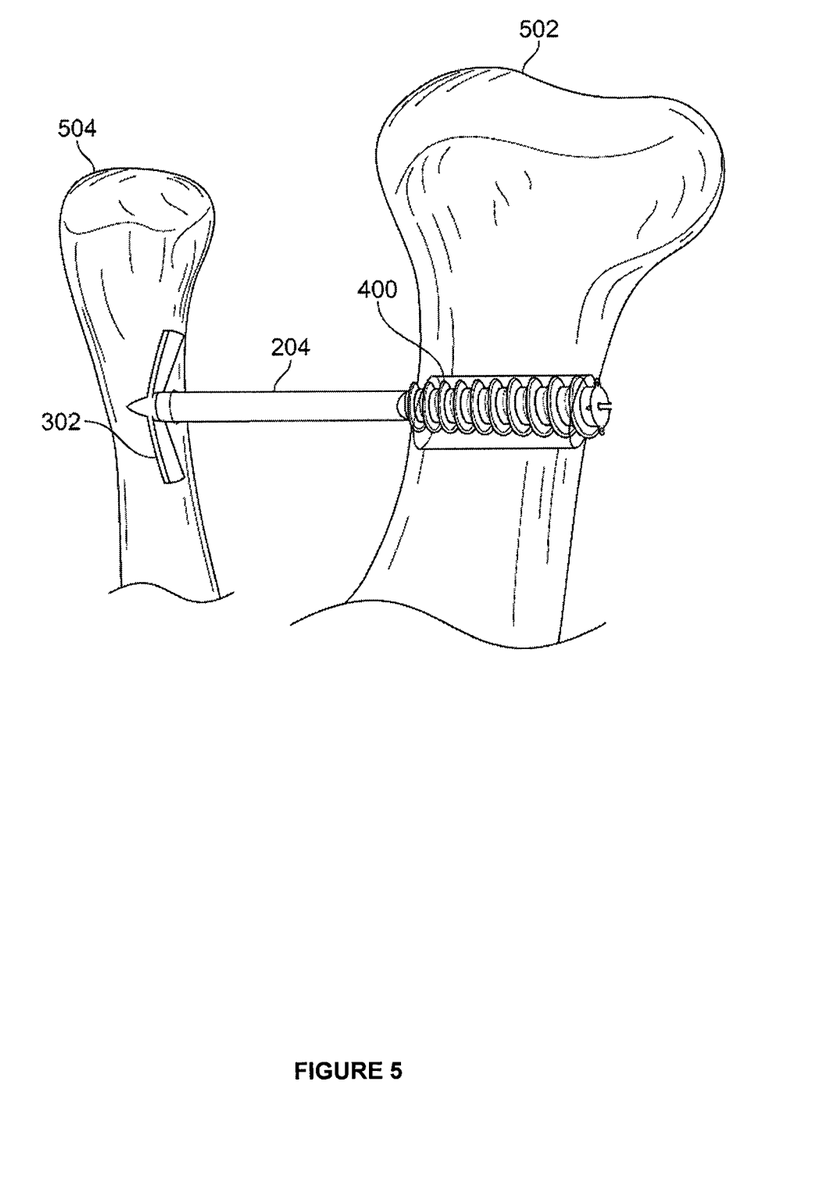
FIG. 5 is a schematic showing the final configuration of the anchoring system of the invention employed for surgical correction of hallux valgus.

Turning to FIG. 5, the final configuration of the anchoring system is schematically shown after a surgical bunion repair, according to principles of the invention such as described above. Here, a proximal first bone 502, a distal second bone 504, anchor region 202, connector region 204, and interference screw 400 are shown. The anchor region 202 with its two expanded arms 302 is embedded within the canal of bone 504, and the connector region 204 extends from the distal second bone 504 and threaded through the through-bore of the interference screw 400 embedded in the proximal first bone 502.

In an alternate embodiment of the invention, the instrument 100 and anchor device 200 may be used to correct or repair other orthopedic conditions, such as mid-foot or tarsometatarsal sprains. The instrument 100 may achieve and may maintain a reduction along the path of the ruptured ligament. After the smaller anchor 200 is set in the second metatarsal, the biomaterial 204 may be used to reconstruct the Lis Franc ligament with the remaining biomaterial 204 secured within the first bone such as the medial cuneiform. The instrument 100 may have the second distal arm centered around the proximal second metatarsal and the first or proximal arm may be placed on the medial cuneiform. Instrument 100 may then assist in performing the reduction of the Lis Franc joint. A drill sleeve 108 with a larger diameter may then be used on the proximal arm to create a tunnel through the medial cuneiform. The drill sleeves with the larger diameter is removed and replaced with a drill sleeve having a smaller diameter. Next, a small pilot hole may be made in the base of the second metatarsal. The anchor 200 may be set into the pilot hole of the second metatarsal and the biocompatible material 204 may be pulled through the medial cuneiform along the anatomic path of the Lis Franc ligament. The biomaterial 204 may then be secured in the medial cuneiform with the interference screw 400.

Figure 6:
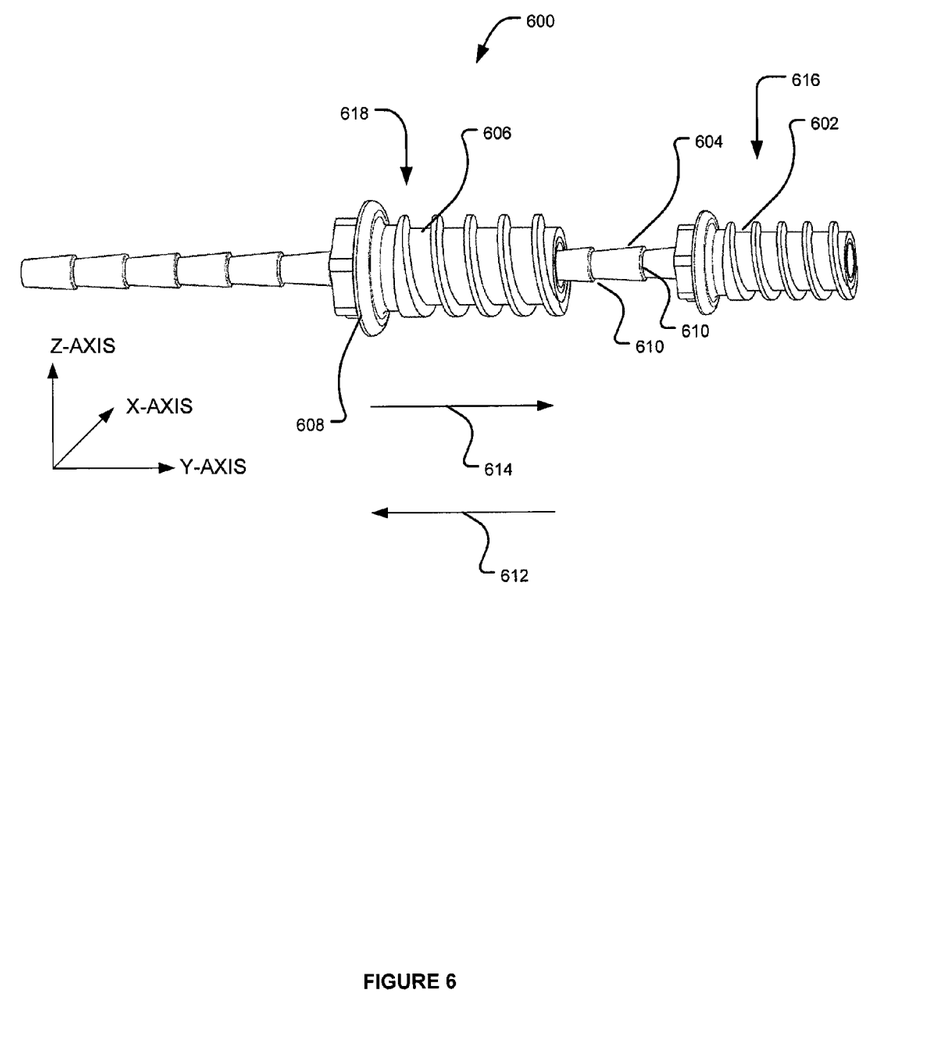
FIG. 6 is a schematic showing one embodiment of the anchoring system of the invention having screw threads as the anchoring mechanism for both the primary and secondary anchors for positioning the anchors relative to each other and a ratcheting mechanism.
Figure 7:
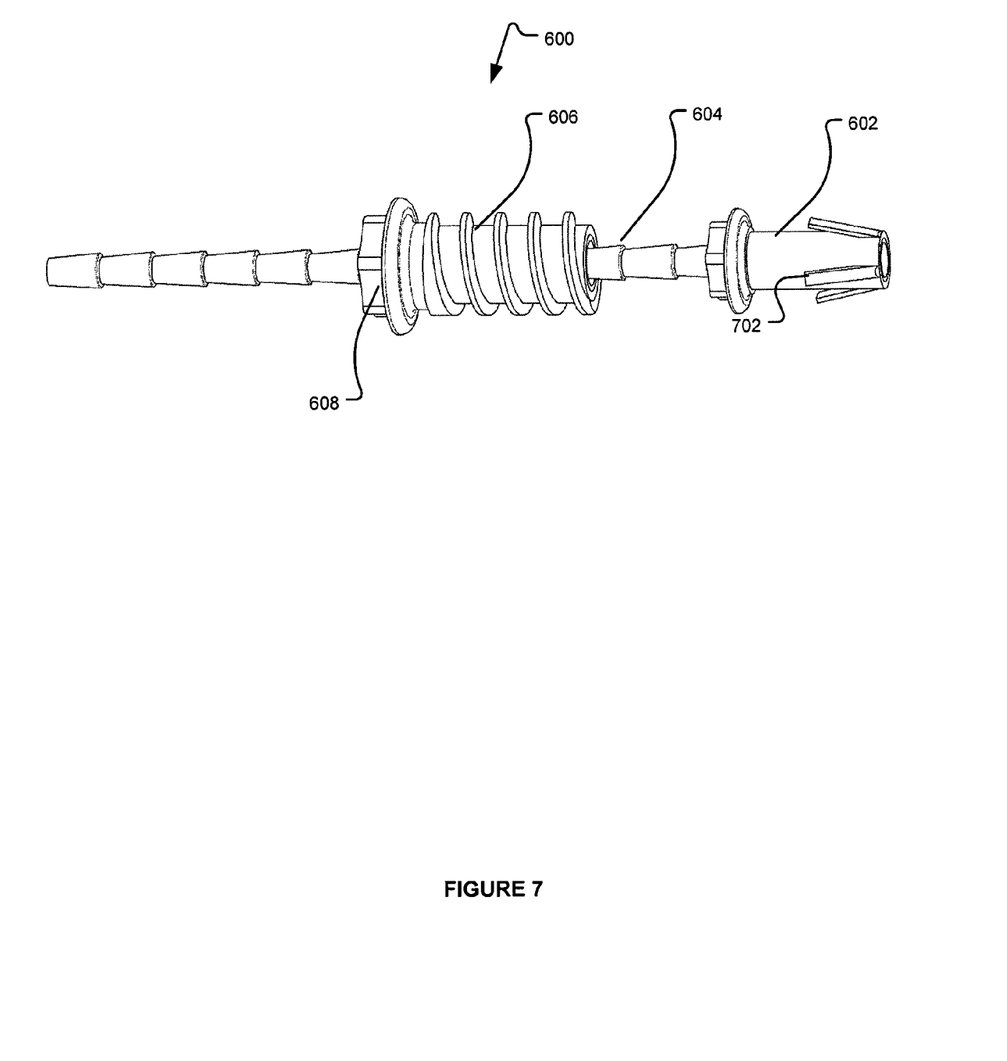
FIG. 7 is a schematic showing one embodiment of the anchoring system of the invention having an expandable material as the locking mechanism of the primary anchor.
Figure 8:
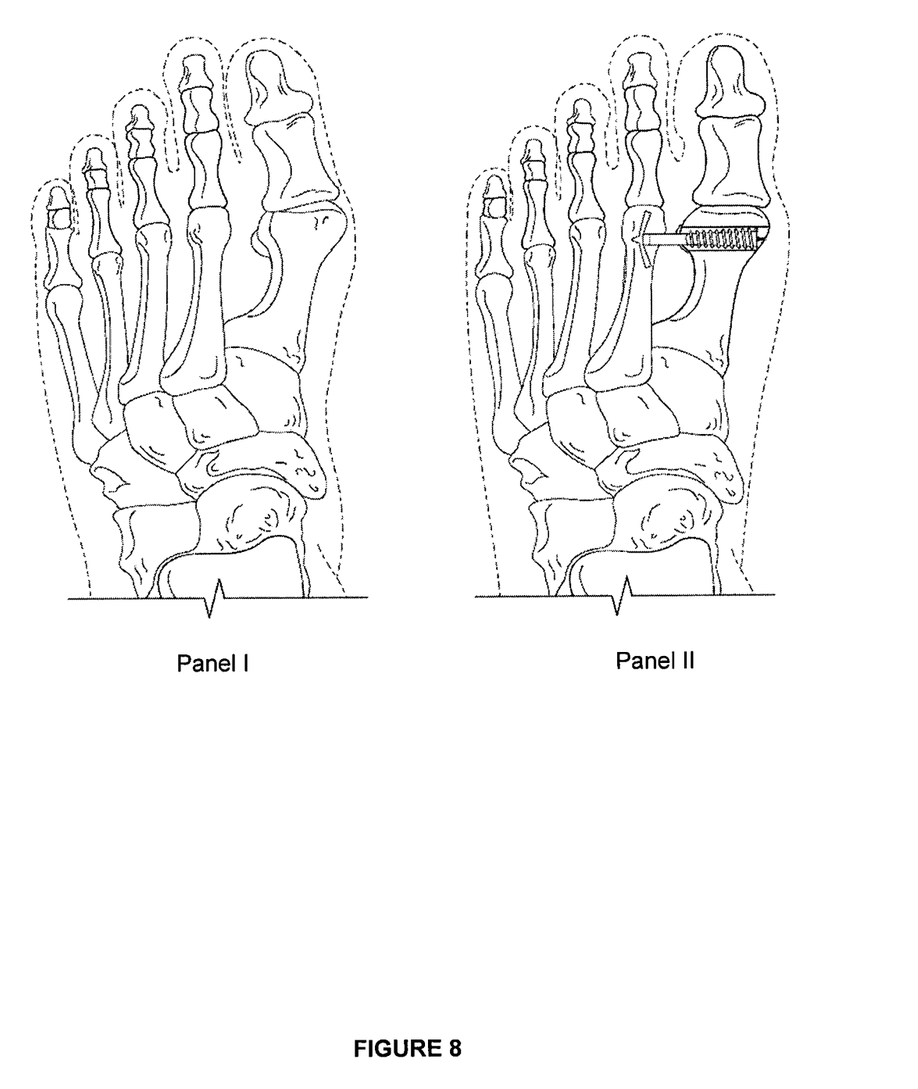
FIG. 8 is a schematic showing a final configuration of the anchoring system FIG. 7 employed for surgical correction of hallux valgus. Panel I shows hallux valgus of the joint of the first metatarsal. Panel II shows correction of hallux valgus of the first metatarsal after correction using the anchoring system of FIG. 7.

According to yet further embodiments of the invention, the anchoring systems illustrated in FIGS. 6-8 may be used for anchoring and stabilizing the first metatarsal via fixation to the second metatarsal. In these embodiments, at least one of the anchors may be disposed on and locked in place on the connector component via a one-way or two-way ratcheting mechanism to achieve precise positioning, as described in more detail below. In FIG. 6, an anchoring system 600 having a distal portion 616, a proximal portion 618, a primary anchor 602, a connection component 604, a proximal secondary anchor 606, and a flange 608 is shown. Anchoring system 600 may be employed using the methods along with device 100, as described above, for fixating the relative position first metatarsal to the second metatarsal and thereby reducing the IM angle of the first metatarsal. The primary anchor 602 and/or the secondary anchor 606 may be bio-absorbable for short-term use or bioactive for long-term tissue integration and/or may also be coated to reduce the potential for infection or to promote tissue in-growth, as described below.

In a specific embodiment, the connection component 604 and secondary anchor 606 may provide for precise relative positioning and locking of the secondary anchor in a number of predetermined positions along the axial length of the connection component via a one-way ratcheting locking mechanism. For example, the outer surface of connection component 604 may have a plurality of spaced protrusions such as angular teeth, ridges, barbs, detents, ribs, or the like, which are adapted to be retained in a mating surface provided on the inside surface of the secondary anchor 606. The mating connections may function to resist motion of the connection component 604 in at least one direction. The locking action formed by the mating connection acts as a one-way ratcheting mechanism. As shown in FIG. 6, the mating connections may be forward facing to facilitate motion of the connection component 604 in one direction 614 while resisting movement of the connection component 604 in a opposite direction 612. Thus, connection component 604 or may have fixed stops precut into the connection component 604 for the secondary anchor 606 to lock against. The ratcheting mechanism thus functions similar to a "cable tie," where a locking component slides over the connection component, adjusting its finished length. In addition, the arrangement of the mating connections may be reversed so the projections may be disposed on the inner surface of the secondary anchor and matingly received in the connection component. Other one-way or two-way locking mechanisms may also be employed such as Velcro type connections or other suitable fabrics.

The position of the secondary anchor 606 may be adjusted by pulling on the connector component to move the component 604 relative to anchor 606 and secure it in place via the locking/ratcheting mechanism. This adjustment could also be accomplished by a variety of mechanical means including winding the connector component onto a screw or using a lever for tension. The ratcheting may be automatic or may be actuated by the user. The ratcheting may be permanent or allow for future adjustment. Thus, the locking device may take the form of a releasable, two-way ratcheting mechanism known in the art. Regardless, the invention should not be construed to be limited to any particular locking or ratcheting mechanism, as these types of mechanisms are well known in the art and can be readily made by techniques known to those of ordinary skill in the art.

The connection component 604 of system 600 may be composed of suture material that may be elastic, braided, or monofilament in nature, or may be a wire, a polymeric strap, or any other suitable ratcheting material. The connection component 604 may be attached directly to one or both anchors or may be attached by an intermediate mechanism. The connection may be asymmetric to provide greater stiffness or flexibility in one direction over another.

The primary anchor 602 and the secondary anchor 606 may be composed of a single body and may be secured into the second metatarsal and first metatarsal, respectively, using such means as screw threads (as shown in FIG. 6), barbs, loops/cuffs, and the like to result in an interference fit. In an alternate embodiment, primary anchor 602 and/or secondary anchor 606 may be composed of a material that expands to lock the anchor in place. For example, FIG. 7 shows system 600 with primary anchor 602 having material 702, connection component 604, and secondary anchor 606. Subsequent to insertion of primary anchor 602 into the second metatarsal, material 702 expands to secure primary anchor 602 in the bone canal of the second metatarsal. FIG. 8 is a schematic illustrating a final configuration of the anchoring system of FIG. 7 (Panel II) for the correction of hallux valgus of the first metatarsal as shown in FIG. 8, Panel I.

Figure 9:
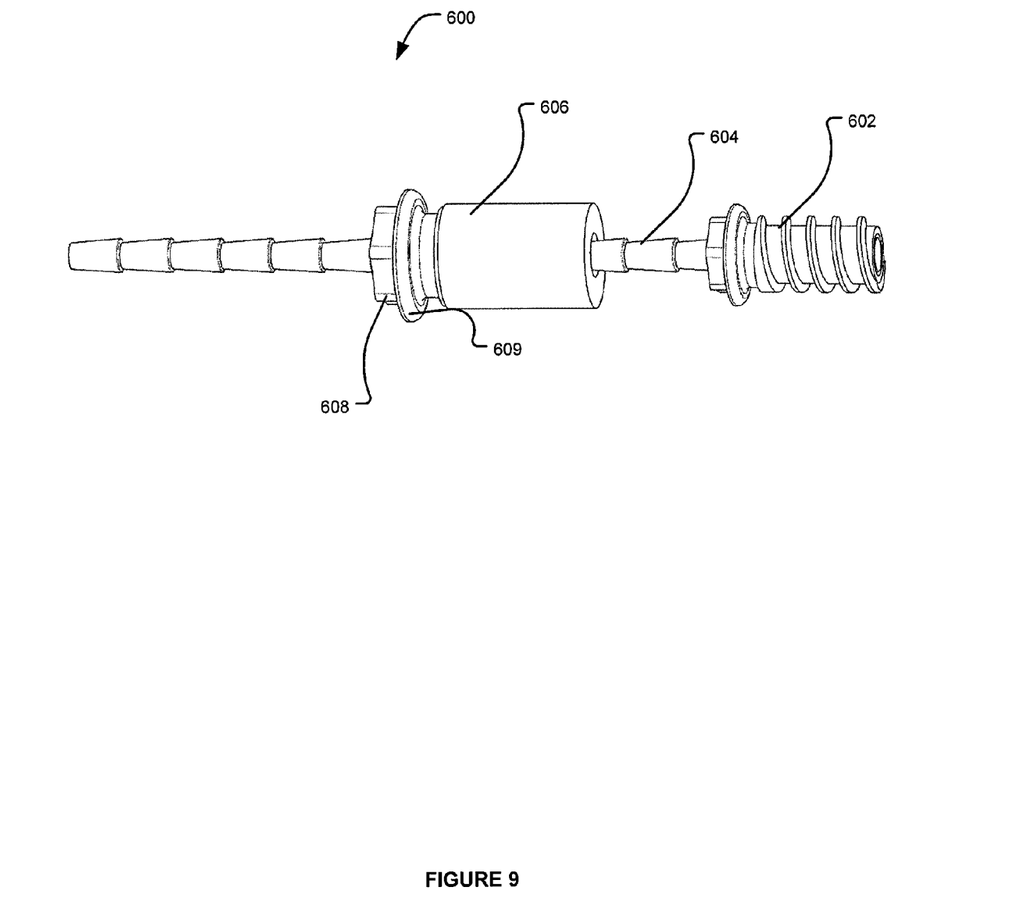
FIG. 9 is a schematic showing one embodiment of the anchoring system of the invention in which the secondary anchor includes a bushing portion disposed inside a bone canal and a flange disposed against the outside of the bone.

FIG. 9 illustrates yet another embodiment of the invention where the secondary anchor 606 is adapted to have a slideable fit within the first metatarsal and/or has an outer dimension that the allows the secondary anchor to act as a bushing to take up the space drilled in the first metatarsal or other bone. For example, secondary anchor 606 may have a smooth outer surface like a washer or a bushing having dimensions selected to slide within the hole drilled in the first metatarsal. The secondary anchor 606 has a flange 608 with a surface 609, which abuts the proximal side of the first metatarsal thereby "sandwiching" the first metatarsal between the secondary anchor 606 and the primary anchor 602 fixed within the bone canal of the second metatarsal.

Alternatively, primary anchor 602 and/or secondary anchor 606 may be connected a linkage to allow for a greater range of motion of the anchoring system, such as a ball joint and/or formed from a somewhat flexible material. In other words, if the axial motion of the anchoring system is along the y-axis of connection component 604, the linkage would permit motion along the x- or z-axis or a combination of x- and z-axes. For example, a ball joint or another type of lost-motion connection may be used to connect the primary anchor 602 and the connection component 604 and/or the connection component and the secondary anchor. This enables the relative position of the metatarsal to be adjusted in all three dimensions.

According to another feature of the invention, bony healing may be induced during the surgical procedure of the invention by introducing bone growth factors such as bone morphogenetic proteins (BMPs) and basic fibroblast growth factor (bFGF) to the target area undergoing correction. These two classes of bone growth factors have been shown to accelerate bone regeneration, bone healing to prosthetic-like implants, and increase strength and stability to the bony callus. The bone growth factors could be delivered to the target area by a variety of methods. One method may be to introduce the bone growth factors in combination with a collagen matrix, which could be a gel- or sponge-like material, to the target area. The bone growth factor may then stimulate the patient's own bone cells into action, while the collagen may provide the scaffolding into which the stimulated bone cells can grow. In the end, bone could replace the collagen scaffold, which may be eventually resorbed.

Another method of delivery may be to coat the anchor screws or interference screws with the bone growth factor in combination with hydroxyapatite, which may have a synergic stimulative effect on the bone cells. For this to be accomplished, an effective amount of the bone growth factor would be absorbed to a gritblasted hydroxyapatite coated anchor or screw prior to implantation into the bone.

However, an alternate method to the delivery of recombinant bone growth factors may be through gene therapy. Delivery by gene therapy may be more cost effective because ex vivo production of DNA for clinical use is inexpensive compared with traditional methods of protein production. Also, gene therapy may be a more efficient way to deliver the bone growth factors compared with traditional protein delivery. One desirable way to utilize gene therapy in the surgical procedure of the invention may be to introduce plasmid-encoded proteins capable of inducing bone growth to the area of distraction. This may be accomplished by introducing biodegradable matrices, such as collagen sponges, containing expression plasmid DNA encoding bone growth factors, also known as gene-activated matrices (GAMs), to the target area.

The description and examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the medical sciences, orthopedic surgery, or related fields are intended to be within the scope of the appended claims.

The disclosures of all references and publications cited above are expressly incorporated by reference in their entireties to the same extent as if each were incorporated by reference individually.

What is claimed is:

1. A surgical method for repair of an orthopedic condition using surgical anchor system comprising a first anchor, a second anchor and a connector, said method comprising:
    fixing the first anchor to a first bone;
    fixing the second anchor to a second bone; and
    connecting the connector to at least one of said first anchor and said second anchor in one of a plurality of predetermined, lockable positions disposed along a length of said connector so that the connector is fixed to said first anchor and said second anchor, said connector being configured to restrain relative movement of said first anchor past a first distance from said second anchor, configured to allow relative movement between said first anchor and said second anchor, and configured to allow a gap between the first bone and the second bone,
    wherein the first bone and the second bone are metatarsals, wherein the connector is configured to restrain relative movement of said first anchor away from said second anchor in a direction along the length of the connector to correct an intermetatarsal angle between the metatarsals, and wherein the connector is configured to allow relative movement of said first and second anchors in plural directions perpendicular to the length of the connector; and
    wherein the connector has only a finite number of the predetermined, lockable positions.

2. The surgical method of claim 1, further comprising delivering said first anchor in a collapsed position to a canal of the first bone and expanding the first anchor within the canal of the first bone to secure the first anchor.

3. The surgical method of claim 1, wherein said first anchor comprises a bioabsorbable material.

4. The surgical method of claim 1, wherein said first anchor comprises a non-absorbable metal.

5. The surgical method of claim 1, wherein said connector comprises a material selected from the group consisting of human dermis, porcine intestinal mucosa, fetal bovine skin, porcine skin, cadaveric fascia, polytetrafluoroethylene, polypropylene, marlex mesh, absorbable suture, non-absorbable suture, and umbilical tape.

6. The surgical method of claim 1, wherein said first anchor is osteogenic.

7. The surgical method of claim 6, wherein the second anchor is osteogenic.

8. The surgical method of claim 1, wherein said first anchor and second anchors are bioabsorbable.

9. The surgical method of claim 1, wherein said first anchor is an osteogenic screw coated with a bone growth factor.

10. The surgical method of claim 1,
    wherein the first bone comprises a first metatarsal, and
    wherein said first anchor comprises a screw, the screw comprising at least one suture receiving portion,
    wherein the method further comprises securing a suture to the suture receiving portion of the screw to reduce a hallux valgus angle of the first metatarsal and a proximal phalanx joined to the first metatarsal.

11. The surgical method of claim 10, further comprising delivering the second anchor in a collapsed configuration to a canal of the second bone and expanding the second anchor to secure the second anchor within the canal of the second bone.

12. The surgical method of claim 1, wherein said first bone is a first metatarsal and said second bone is a second metatarsal.

13. The surgical method of claim 1,
    wherein the first bone is a first metatarsal, and
    wherein the method further comprises securing a suture to a suture receiving portion of said first anchor to reduce a hallux valgus angle of the first metatarsal and a proximal phalanx joined to the first metatarsal.

14. The surgical method of claim 1, further comprising positioning a first portion of the second anchor to grip the second bone along a length of the first portion and to extend from a first wall of the second bone to a second wall of the second bone opposite the first wall of the second bone.

15. The surgical method of claim 14, wherein the first portion is a screw.

16. The surgical method of claim 15, wherein the second anchor is an interference screw.

17. The surgical method of claim 14, wherein the first portion has a smooth outer surface.

18. The surgical method of claim 1, wherein the connector has a first fixed connection to the first anchor and a second fixed connection to the second anchor.

19. The surgical method of claim 1, wherein the connector is connected to said first anchor and said second anchor to secure the reduction of an angle between the first bone and the second bone.

20. The surgical method of claim 1, wherein the connector is configured to allow movement of said first and second anchors in a direction towards each other.

21. The surgical method of claim 1, wherein the connector is configured to restrain movement of said first and second anchors in a direction towards each other.

22. A surgical method for repair of an orthopedic condition using a surgical anchor system comprising a first anchor a second anchor and a connector the method comprising:
  inserting the first anchor into a first bone;
  inserting the second anchor into a second bone; and
  connecting the connector to at least one of said first anchor and said second anchor in one of a plurality of predetermined, lockable positions disposed along a length of said connector so that the connector extends between said first and second anchors, allows a gap between the first bone and the second bone, prevents an enlargement of the gap between the first bone and second bone beyond a first distance, and allows relative movement between the first bone and second bone,
  wherein the first bone and the second bone are metatarsals, wherein the connector is configured to restrain relative movement of said first anchor away from said second anchor in a direction along the length of the connector to correct an intermetatarsal angle between the metatarsals, and wherein the connector is configured to allow relative movement of said first and second anchors in plural directions perpendicular to the length of the connector; and
  wherein the connector has only a finite number of the predetermined, lockable positions.

23. The surgical method of claim 22, wherein said connector mates with an interior surface of at least one of said first anchor and said second anchor.

24. The surgical method of claim 22, further comprising in the first anchor to the first bone by at least one of screw threads, barbs, loops, and cuffs.

25. The surgical method of claim 22, further comprising expanding moveable arms of the first anchor within a canal of the first bone to fix said first anchor to the first bone.

26. The surgical method of claim 22, wherein said second anchor is fixedly attached to the second bone by at least one of screw threads, barbs, loops, and cuffs.

27. The surgical method of claim 22, further comprising inserting a first portion of said second anchor into the second bone while a second portion of said second anchor is disposed against an outer surface of the second bone.

28. The surgical method of claim 22, wherein the first bone is a second metatarsal and the second bone is a first metatarsal.

29. The surgical method of claim 22, wherein said first anchor and said second anchor comprise a bioabsorbable material.

30. The surgical method of claim 22, wherein said first anchor and said second anchor comprise a non-bioabsorbable metal.

31. The surgical method of claim 22, wherein said first anchor and said second anchor are osteogenic.

32. The surgical method of claim 22, wherein said connector comprises a material selected from the group consisting human dermis, porcine intestinal mucosa, fetal bovine skin, porcine skin, cadaveric fascia, polytetrafluorethylene, polypropylene, marlex mesh, absorbable suture, non-absorbable, and umbilical tape.

33. The surgical method of claim 22, wherein said connector is pivotally attached to at least one of said first anchor and said second anchor.

34. The surgical method of claim 22,
  wherein the first bone comprises a first metatarsal, and the method further comprises:
  using said first anchor to reduce a hallux valgus angle of a first metatarsal and a proximal phalanx joined to the first metatarsal.

35. The surgical method of claim 22, further comprising delivering at least one of said first anchor and said second anchor in a collapsed configuration into a canal of the respective first or second bone and expanding the at least one of said first anchor and said second anchor to secure the anchor within the canal of the respective first or second bone.

36. The surgical method of claim 22, wherein the connector is a ratcheting component.

37. The surgical method of claim 22, wherein the connector is flexible.

38. The surgical method of claim 37, wherein the connector is configured to allow movement of said first and second anchors in a direction towards each other.

39. The surgical method of claim 37, wherein the connector is configured to restrain movement of said first and second anchors in a direction towards each other.

40. The surgical method of claim 22, wherein further comprising positioning a first portion of the second anchor to grip the second bone along a length of the first portion, and to extend from a first wall of the second bone to a second wall of the second bone opposite the first wall of the second bone.

41. A surgical method for repair of an orthopedic condition using surgical anchor system comprising a first anchor, a second anchor and a connector, said method comprising:
  fixing the first anchor to a first metatarsal;
  fixing the second anchor to a second metatarsal; and
  connecting the connector to at least one of said first anchor and said second anchor in one of a plurality of predetermined, lockable positions disposed along a length of said connector so that the connector is connected to said first anchor and said second anchor, said connector securing a reduction of an angle between the first metatarsal and the second metatarsal while allowing relative movement between said first metatarsal and said second metatarsal,
  wherein the connector restrains relative movement of said first anchor away from said second anchor in a direction along the length of the connector while allowing relative movement of said first and second anchors in plural directions perpendicular to the length of the connector; and
  wherein the connector has only a finite number of the predetermined, lockable positions.

42. The surgical method of claim 41, wherein the first anchor is positioned to extend from a first wall of the first metatarsal to a second wall of the first metatarsal, through a canal of the first metatarsal.

43. The surgical method of claim 42, wherein the second anchor is positioned to extend from a first wall of the second metatarsal to a second wall of the second metatarsal, through a canal of the second metatarsal.

44. The surgical method of claim 41, wherein the connector has a first fixed connection to the first anchor and a second fixed connection to the second anchor.

\* \* \* \* \*